(12) United States Patent
Friedhoff et al.

(10) Patent No.: US 6,455,544 B1
(45) Date of Patent: Sep. 24, 2002

(54) USE OF CHOLINESTERASE INHIBITORS TO TREAT DISORDERS OF ATTENTION

(75) Inventors: Lawrence T. Friedhoff, Rivervale, NJ (US); Paul J. Tiseo, New York, NY (US); Sharon L. Rogers, New York, NY (US)

(73) Assignee: Eisai Co. Ltd., Tokyo (JP)

( * ) Notice: Subject to any disclaimer, the term of this patent is extended or adjusted under 35 U.S.C. 154(b) by 0 days.

(21) Appl. No.: 09/033,880

(22) Filed: Mar. 3, 1998

Related U.S. Application Data

(60) Provisional application No. 60/039,832, filed on Mar. 3, 1997.

(51) Int. Cl.[7] ...................... A61K 31/445; A61K 31/55; A61K 31/40
(52) U.S. Cl. ...................... 514/319; 514/212; 514/408
(58) Field of Search ................... 514/319, 212, 514/408

(56) References Cited

U.S. PATENT DOCUMENTS 5,064,858 A * 11/1991 Sapse .................. 514/536
6,113,879 A *  9/2000 Richards et al. ............ 429/91

FOREIGN PATENT DOCUMENTS

WO    WO97/46527 A1    12/1997

OTHER PUBLICATIONS

Medline Abstract, AN: 97072226, Rogers et al., 1997.*
Biosis Abstract, AN: 1997:160992, Yamamoto et al. 1997.*
Rogers et al, Dementia, 7(6):293–303 (1996).
Yamamoto, Behavioural Brain Research, 83:57–62 (1997).
Mannuzz et al, "Adult Outcome of Hyperactive Boys," Arch. Gen. Psychiatry, 50:565–576 (Jul. 1993).
Safer et al, "A Survey of Medication Treatment for Hyperactive/Inattentive Students," JAMA, 260(15):2256–2258 (1988).
Diagnostic and Statistical Manual of Mental Disorders, 4th Ed., Text Revision, pp. 85–93 and 147–158 (2000).
Kirkby et al., *Behavioural Pharmacology*, 7:513–525, 1996.

* cited by examiner

Primary Examiner—Russell Travers
Assistant Examiner—Shengjun Wang
(74) Attorney, Agent, or Firm—Hale and Dorr LLP

(57) ABSTRACT

The present invention provides novel methods of treating disorders of attention or improving attention in humans by administering an effective amount of a cholinesterase inhibitor.

14 Claims, No Drawings

USE OF CHOLINESTERASE INHIBITORS TO TREAT DISORDERS OF ATTENTION

This application claims priority under 35 U.S.C. §119 from provisional application Serial No. 60/039,832, filed Mar. 3, 1997, which is herein incorporated by reference in its entirety.

FIELD OF THE INVENTION

This invention relates to the use of cholinesterase inhibitor compounds for treatment of disorders of attention, such as Attention Deficit Disorder (ADD). The compounds are also useful as a replacement for other substances which patients commonly use to self-medicate for these disorders, and which can have undesirable side effects.

BACKGROUND OF THE INVENTION

Disorders of attention are a significant public health problem. Primary attention deficit disorder is estimated to affect 6 to 9 percent of school aged children (Anderson, J. C. et al. *Arch. Gen. Psych.* 44:69 (1987); Safer, D. J. et al. *JAMA* 260:2256 (1988)). Well-designed follow-up studies have demonstrated that this disorder is not confined to childhood but is present in up to 50 percent of young adults who have the disorder as children (Mannuzza, S. et al. *Arch. Gen. Psych.* 50:565; Willens, T. E. et al. In Nadeau, K. Ed. *A Comprehensive Guide to Attention Deficit Disorder*, Brunne/Mazel, Inc. New York, (1993). This suggests that up to 2 to 4 percent of the adults in the United States may exhibit symptoms of a primary attention deficit disorder. Disorders of attention often lead to poor performance in school and at work and are correlated with antisocial behavior. These behaviors carry a high cost to individuals in lost time and effort, as well as imposing direct costs on society.

Attention disorders are also associated with indirect costs. For example, there is evidence that patients with attention disorders often "self-medicate" in destructive ways. These patients have a higher than average incidence of cigarette smoking and alcoholism. They also have a higher than average incidence of illegal drug use (Barkley, R. A. In *Attention Deficit Hyperactivitiy Disorder*, Guilford Press, New York, (1990) Chapter 4, pp. 106–129). Thus, an effective treatment for attention disorders would be also be a useful treatment for some substance dependencies.

Current approved treatments for attention deficit disorder are limited to drugs that affect amine metabolism in the brain (Spencer, T. et al. *J. Am. Acad. Child Adolesc. Psych.* 35:409 (1996)). These drugs have significant limitations including side effects and abuse potential, making currently available treatments controversial. Such medications include the stimulants methylphenidate and dextroamphetamine. Pemoline is another stimulant sometimes used to treat attention deficit disorder in children. These stimulant drugs can have cardiac side effects, which are less pronounced in the case of methylphenidate. These stimulants can also cause growth suppression in children, and are potentially addictive for adolescents and adults.

Current alternatives to stimulants for the treatment of attention disorders are the tricyclic antidepressants and clonidine. The use of tricyclic antidepressants is more likely than the use of stimulants to cause cardiac arrhythmias in children. However, because of the likelihood of stimulant abuse by adolescents and adults with attention disorders, tricyclic antidepressants and clonidine are often tried first (Maxmen, J. S. and Ward, N. G. *Essential Psychopathology and Its Treatment*, p. 443, Second Edition, Norton & Co., New York, (1995)).

Recent studies have shown that nicotine may be an effective treatment for attention deficit disorder (Levin, E. D. et al. *Psychopharmacology* 123:55 (1996)). However, nicotine acts at multiple pharmacological sites in the body, can be addictive and also has undesirable side effects, and its mode of action is not known. It is not known, for example, which of nicotine's pharmacological effects are responsible for the increased attention displayed by subjects to whom nicotine was administered.

Impaired attention may also be a characteristic of Alzheimer's disease, although Alzheimer's patients typically remain alert (Coyle et al., Alzheimer's Disease: A Disorder of Cholinergic Innervation, *Science* 219:1184–90 (1983)), and the underlying disorders and known treatments are very different (Grady, C. L. et al. *J. Clin. Exp. Neuropsychology* 10:576 (1988)). Alzheimer's disease involves progressive and profound loss of memory, postulated to involve a deficiency in brain cortical acetylcholine affecting cholinergic synapses. This deficiency is thought to be caused by selective degeneration of acetylcholine-releasing neurons (Coyle, supra). Disorders of attention and ADD, which are concerned with mental concentration as opposed to memory, are not thought to be caused by acetylcholine defficiencies.

Certain synapses of the brain use acetylcholine as a neural transmitter, to transmit messages across the synapse to a cholinergic receptor. During normal transmission, acetylcholine crosses the synaptic gap to carry the message by stimulating the cholinergic receptor. Memory is thought to be related, at least in part, to post-synaptic changes which occur as a result of the timing and strength of acetylcholine stimulation during learning, with certain experiences tending to block or facilitate corresponding neural pathways, i.e. making it more or less difficult to stimulate the same post-synaptic receptor at a future time (Deutsch, The Cholinergic Synapse and the Site of Memory, *Science* 174:788–94 (1971)). Acetylcholine also is rapidly destroyed by the enzyme cholinesterase. Thus, insufficient acetylcholine or excess cholinesterase can interfere with synaptic transmission by too rapidly destroying the acetylcholine message, resulting in weak cholinergic stimulation which can be experienced as memory loss. When this condition is chronic, i.e. from degeneration of acetylcholine-releasing neurons, the Alzheimer's syndrome may develop. One way of counteracting this imbalance is by interfering with the ability of cholinesterase to degrade acetylcholine, as by treatment with a cholinesterase inhibitor (Sugimoto et al., U.S. Pat. No. 4,895,841).

Attention is related to memory in that attention is a prerequisite to memory. Disorders of attention or learning, including ADD, do not typically involve memory loss, and are characterized by symptoms such as motor restlessness, short attention span, poor concentration and organizational skills, impulsive behavior, and lack of task persistence. The cause or causes of ADD is unknown. Several theories have been proposed, and include impaired ability of the frontal lobes to process current experiences and integrate them with memory (frontal lobe disinhibition), as well as abnormalities or imbalances in one or more of dopamine and norepinephrine in the brain (the catecholemine hypothesis). However, studies of these catecholamines in both animals and man, as well as other neurotransmitters such as serotonin, have yielded inconsistent results regarding the biochemical basis for ADD. Although impaired use of dopamine, norepinephrine, and serotonin is implicated in ADD, the underlying neurochemical dysfunction is not well understood, nor are there satisfactory and well-recognized therapies for ADD.

Thus, a need exists for additional therapies which effectively treat disorders of attention generally, and ADD specifically. Therapies which are specific to loss of attention, and which are not addictive, do not promote cardiac imbalance, and do not have other undesirable characteristics are particularly needed.

SUMMARY OF THE INVENTION

It has now been surprisingly discovered that augmentation of cholinergic transmission is an effective treatment for attention deficit disorder. It has also been discovered that the compounds of this invention are useful for the treatment of disorders of attention, including attention deficit disorder.

Cholinesterase inhibitors provide one method of augmenting cholinergic transmission. They tend to be associated with fewer side effects than other methods because they augment the effects of endogenous acetylcholine rather than acting directly. Additionally, cholinesterase inhibitors are more specific to areas of the body where endogenous acetylcholine is being released. They have a longer duration of action than nicotine, which is rapidly metabolized. Donepezil hydrochloride and its congeners are cholinesterase inhibitors that offer the additional advantage of specificity for acetylcholinesterase, the predominant form of the enzyme in the brain. For example, donepezil hydrochloride has approximately 1200-fold specificity for acetylcholinesterase relative to butyrlcholinesterase, the most common cholinesterase outside the brain and central nervous system.

The present invention provides novel methods of treating disorders of attention in humans by administering an effective amount of a cholinesterase inhibitor. More particularly, the invention provides a method for treating disorders of attention by administering to a human in need of such treatment an effective amount of a compound of the formula:

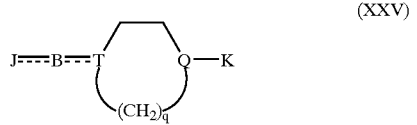

(XXV)

in which J is
  (a) a group, substituted or unsubstituted, selected from the group consisting of (1) phenyl, (2) pyridyl, (3) pyrazyl, (4) quinolyl, (5) cyclohexyl, (6) quinoxalyl and (7) furyl;
  (b) a monovalent or divalent group, in which the phenyl may have a substituent(s), selected from the group consisting of (1) indanyl, (2) indanonyl, (3) indenyl, (4) indenonyl, (5) indanedionyl, (6) tetralonyl, (7) benzosuberonyl, (8) indanolyl and (9) $C_6H_5$—CO—CH($CH_3$)—;
  (c) a monovalent group derived from a cyclic amide compound;
  (d) a lower alkyl or
  (e) a group of $R^{21}$—CH=CH— in which $R^{21}$ is hydrogen or a lower alkoxycarbonyl;
B is —$(CHR^{22})_r$—, —CO—$(CHR^{22})_r$—, —$NR^4$—$(CHR^{22})_r$—, $R^4$ being hydrogen, a lower alkyl, an acyl, a lower alkylsulfonyl, phenyl, a substituted phenyl, benzyl or a substituted benzyl, —CO —$NR^5$—$(CHR^{22})_r$—, $R^5$ being hydrogen, a lower alkyl or phenyl, —CH=CH—$(CHR^{22})_r$—, —OCOO—$(CHR^{22})_r$—, —OOC—NH—$(CHR^{22})_r$—, —NH—CO—$(CHR^{22})_r$—, —$CH_2$—CO—NH—$(CH^{22})_r$—, —$(CH_2)_2$—NH—$(CHR^{22})_r$—, —CH(OH)—$(CHR^{22})_r$—, r being zero or an integer of 1 to 10, $R^{22}$ being hydrogen or methyl so that one alkylene group may have no methyl branch or one or more methyl branch, =(CH—CH=CH)$_b$—, b being an integer of 1 to 3, =CH—$(CH_2)_c$—, c being zero or an integer of 1 to 9, =(CH—CH)$_d$=, d being zero or an integer of 1 to 5; —CO—CH=CH—$CH_2$—, —CO—$CH_2$—CH(OH)—$CH_2$—, —CH($CH_3$)—CO—NH—$CH_2$—, —CH=CH—CO—NH—$(CH_2)_2$—, —NH—, —O—, —S—, a dialkylaminoalkylcarbonyl or a lower alkoxycarbonyl;

T is a nitrogen or carbon;
Q is nitrogen, carbon or

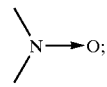

and q is an integer of 1 to 3;
K is hydrogen, phenyl, a substituted phenyl, an arylalkyl in which the phenyl may have a substituent, cinnamyl, a lower alkyl, pyridylmethyl, a cycloalkylalkyl, adamantanemethyl, furylmenthyl, a cycloalkyl, a lower alkoxycarbonyl or an acyl; and === shows a single bond or a double bond.

In the compounds having the formula (XXV), it is preferable that J is (a) or (b). In the definition (b), monovalent groups of (2), (3) and (5) and divalent groups of (2) are preferable. In the definition of B, —$(CHR^{22})_r$—, =(CH—CH=CH)$_b$—, =CH—$(CH_2)_c$— and =(CH—CH)$_d$= are preferable. These preferable groups of (B) may be connected with (b) of J, in particular (2) of (b).

It is preferable in the formula (XXV) that Q is nitrogen, T is carbon and q is 1 or 3; and Q is carbon, T is nitrogen and q is 2. It is most preferable that Q is nitrogen, T is carbon and q is 2.

It is preferable that K is a phenylalkyl or a phenylalkyl having a substituent(s) on the phenyl.

Preferable compounds have the above shown formula in which J is (b). The group (b) includes ten groups having the respective formulae shown below. S is hydrogen or a substituent such as a lower alkyl having 1 to 6 carbon atoms and a lower alkoxy having 1 to 6 carbon atoms and t is an integer of 1 to 4. Among the substituents, methoxy is most preferred. The phenyl is most preferred to have 1 to 3 methoxy groups. (S)$_t$ may form a methylene dioxy group or ethylene dioxy group on two adjacent carbon atoms of the phenyl group.

A preferable definition of B includes —$(CHR^{22})_r$—, —CO—$(CHR^{22})_r$—, =(CH—CH=CH)$_b$—, =CH—$(CH_2)_c$— and =(CH—CH)$_d$=. The group —$(CHR^{22})_r$— in which $R^{22}$ is hydrogen and r is an integer of 1 to 3 and then the group =CH—$(CH_2)_c$— are most preferable.

In the above defined cyclic amine compounds of the methods of the invention, it is preferable that J in the formula is (b), the monovalent or divalent group. In the definition (b), indanonyl, indanedionyl and indenyl are most preferable, optionally having one or more substituents on the phenyl.

In the definition B, —$(CHR^{22})_r$— and =CH—$(CH2)_c$— are preferable.

The ring including T and Q may be a 5-, 6- or 7-membered ring. It is preferable that Q is nitrogen, T is carbon or nitrogen and n is 2; Q is nitrogen, T is carbon and n is 1 or 3; and Q is carbon, T is nitrogen and n is 2.

In the definition K, phenyl, an arylalkyl and cinnamyl are preferable, optionally having one or more substituents on the phenyl.

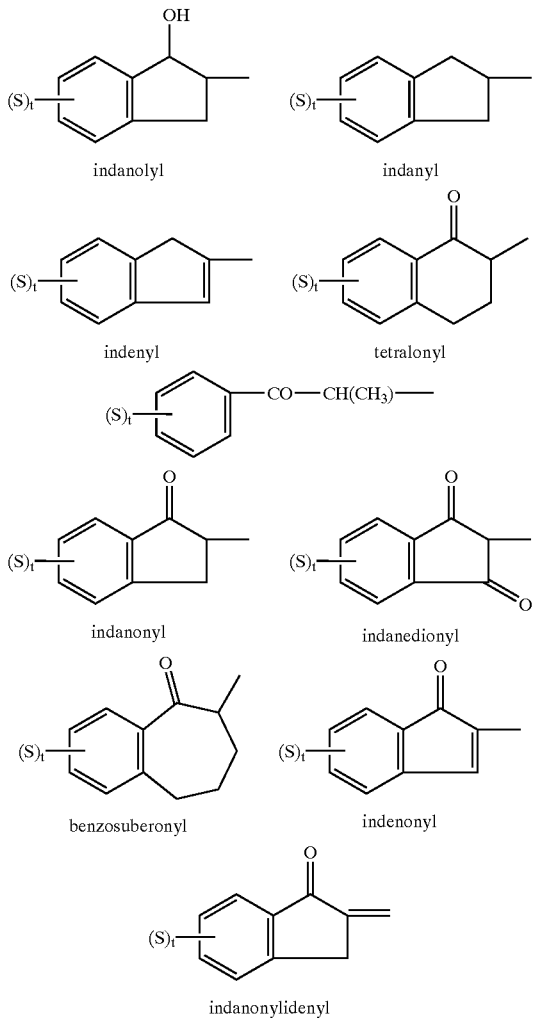

More preferably, the method comprises treating disorders of attention by administering an effective amount of a compound selected from the group consisting of:
1-benzyl-4-((5,6-dimethoxy-1-indanon)-2-yl) methylpiperidine,
1-benzyl-4-((5,6-dimethoxy-1-indanon)-2-ylidenyl) methylpiperidine,
1-benzyl-4-((5-methoxy-1-indanon)-2-yl)methylpiperidine,
1-benzyl-4-((5,6-diethoxy-1-indanon)-2-yl) methylpiperidine,
1-benzyl-4-((5,6-methnylenedioxy-1-indanon)-2-yl) methylpiperidine,
1-(m-nitrobenzyl)-4-((5,6-dimethoxy-1-indanon)-2-yl) methylpiperidine,
1-cyclohexymethyl-4-((5,6-dimethoxy-1-indanon)-2-yl) methylpiperidine,
1-(m-florobenzyl)-4-((5,6-dimethoxy-1-indanon)-2-yl) methylpiperidine,
1-benzyl-4-((5,6-dimethoxy-1-indanon)-2-yl) propylpiperidine,
1-benzyl-4-((5-isopropoxy-6-methoxy-1-indanon)-2-yl) methylpiperidine and
1-benzyl-4-((5,6-dimethoxy-1-oxoindanon)-2-yl) propenylpiperidine.

Most preferably, the method comprises treating disorders of attention by administering an effective amount of the compound 1-benzyl-4-((5,6-dimethoxy-1-indanon)-2-yl) methylpiperidine.

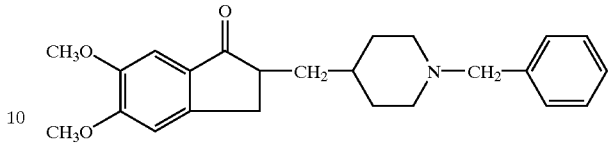

DETAILED DESCRIPTION OF THE INVENTION

The invention is explained in detail in view of the piperidine compounds which fall within the scope of the above defined cyclic amine compound. It will be understood, however, that this explanation applies to the use of the entire group of cyclic amine compounds for the treatment of attention disorders.

The piperidine compounds of the methods of the invention are defined by the formula (I):

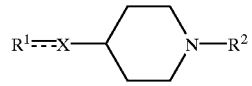

wherein $R^1$ is the following substituted or unsubstituted group: 1) a phenyl group, 2) a pyridyl group, 3) a pyrazyl group, 4) a quinolyl group, 5) an indanyl group, 6) a cyclohexyl group, 7) a quinoxalyl group, or 8) a furyl group; a monovalent or divalent group derived from an indanone having an unsubstituted or substituted phenyl ring; a monovalent group derived from a cyclic amide compound; a lower alkyl group or a group represented by the formula $R^3$—CH=C— (wherein $R^3$ is a hydrogen atom or a lower alkoxycarbonyl group), X is a member selected from the group represented by the formulas

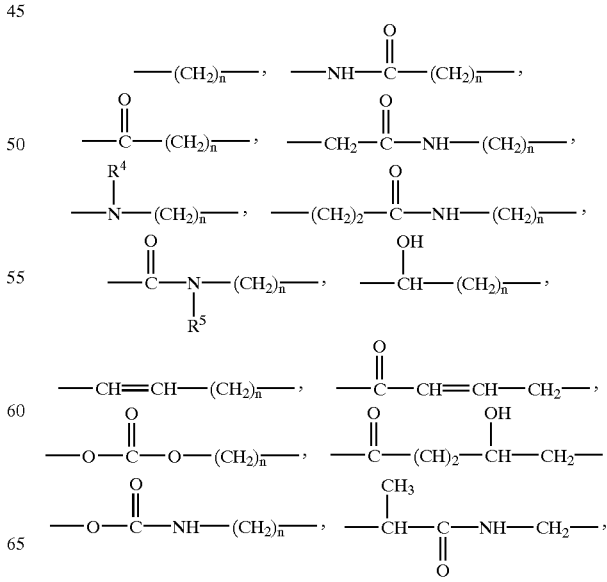

-continued

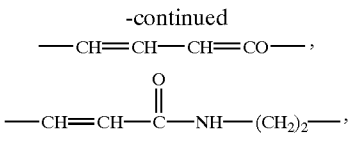

a dialkylaminoalkylcarbonyl group, and a lower alkoxycarbonyl group, wherein $R^4$ is a hydrogen atom, a lower alkyl group, an acyl group, a lower alkylsulfonyl group, or a substituted or unsubstituted phenyl or benzyl and $R^5$ is a hydrogen atom, a lower alkyl group, or a phenyl group, and wherein the n's in the above definition of X are each independently an integer of 0 to 6, $R^2$ is a substituted or unsubstituted phenyl group, a substituted or unsubstituted arylalkyl group, a cinnamyl group, a lower alkyl group, a pyridylmethyl group, a cycloalkylalkyl group, an adamantanemethyl group, or a furoylmethyl group, and the symbol, ==== means a single bond or a double bond.

The term "lower alkyl group" used in the above definition of $R^1$, $R^2$, $R^4$ and $R^5$ with respect to the compound (I) of the present invention is intended to mean a straight-chain or branched alkyl group having 1 to 6 carbon atoms, and examples thereof include methyl, ethyl, propyl, isopropyl, butyl, isobutyl, sec-butyl, tert-butyl, pentyl (amyl), isopenthyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimenthylbutyl, 2,2-diinethylbutyl, 1,3-dimethylbutyl, 2,3-dimenthylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl groups. Among these, methyl, ethyl, propyl, and isopropyl groups are preferable. A methyl group is the most preferable.

Examples of the substituents (1)–(8) in the definition of $R^1$ above include lower alkyl groups having 1 to 6 carbon atoms, such as methyl, ethyl, n-propyl, isopropyl, n-butyl, isobutyl, and tert-butyl groups; lower alkoxy groups corresponding to the above-described lower alkyl groups, such as methoxy and ethoxy groups; a nitro group; halogen atoms such as chlorine, bromine, and fluorine; a carboxyl group; lower alkoxycarbonyl groups corresponding to the above-described lower alkoxy groups, such as methoxycarbonyl, ethoxycarbonyl, isopropoxycarbonyl, n-propoxycarbonyl, and n-butyloxycarbonyl groups; an amino group; a lower monoalkylamino group; a lower dialkylamino group, a carbamoyl group; acylamino groups derived from aliphatic saturated monocarboxylic acids having 1 to 6 carbon atoms, such as acetylamino, propionylamino, butyrylamino, isobutyrylamino, valerylamino, and pivaloylamino groups; cycloalkyloxycarbonyl groups such as a cyclohexyloxycarbonyl group; lower alkylaminocarbonyl groups such as methylaminocarbonyl and ethylaminocarbonyl groups; lower alkylcarbonyloxy groups corresponding to the above-defined lower alkyl groups, such as methylcarbonyloxy, ethylcarbonyloxy, and n-propylcarbonyloxy groups; halogentated lower alkyl groups including a trifluoromethyl group; a hydroxyl group; a formyl group; and lower alkoxy lower alkyl groups such as ethoxymethyl, methoxymethyl, and methoxyethyl groups. The "lower alkyl groups" and "lower alkoxyl groups" in the above description of the substituent include all the groups derived from the above-mentioned groups. The substitutent may be one to three of them which may be the same or different.

When the substitutent is a phenyl group, the following group is within the scope of the substituted phenyl group:

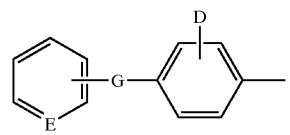

wherein G is a member of a group selected from the formulas —O—, —CH$_2$—O—, —CH$_2$—SO$_2$—,

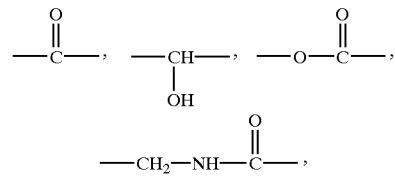

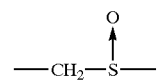

and a group represented by the formula $$-CH_2-\overset{O}{\underset{\uparrow}{S}}-$$

and E is a carbon or nitrogen atom.

Preferable examples of the substituents for the phenyl group include lower alkyl, lower alkoxy, nitro, halogenated lower alkyl, lower alkoxycarbonyl, formyl, hydroxyl, and lower alkoxy lower alkyl groups, halogen atoms, and benzoyl and benzylsulfonyl groups. The substituent may be two or more of them which may be the same or different.

Preferable examples of the substituent for the pyridyl group include lower alkyl and amino groups and halogen atoms.

Preferable examples of the substituent for the pyrazyl group include lower alkoxycarbonyl, carboxyl, acylamino, carbamoyl, and cycloalkyloxycarbonyl groups.

With respect to $R^1$, the pyridyl group is preferably a 2-pyridyl, 3-pyridyl, or 4-pyridyl group; the pyrazyl group is preferably a 2-pyrazinyl group; the quinolyl group is preferably a 2-quinolyl or 3-quinolyl group; the quinoxalinyl group is preferable a 2-quinoxalinyl or 3-quinoxalinyl group; and the furyl group is preferably a 2-furyl group.

Specific examples of preferable monovalent or divalent group derived from an indanone having an unsubstituted or substituted phenyl ring include those represented by the following formulae (II) and (III):

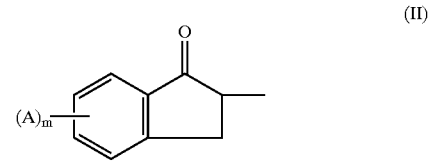

(II)

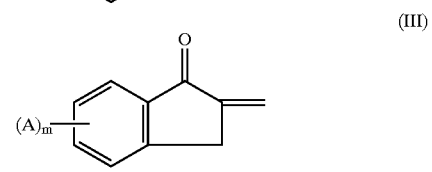

(III)

wherein each m is an integer from 1 to 4 and each A, which may be the same or different, is one of the substituents described in the above items (1) to (8) of the definition of $R^1$ or a hydrogen atom, preferably a hydrogen atom (i.e. unsubstituted), a lower alkyl group, or a lower alkoxy group, and most preferably the indanone group is unsubstituted or substituted with 1 to 3 methoxy groups.

Examples of the monovalent group derived from a cyclic amide compound include quinazolone, tetrahydroisoquinolinone, tetrahydrobenzodiazepinone, and hexahydrobenzazocinone. However, the monovalent group may be any one having a cyclic amide group in the structural formula thereof and is not limited to the above-described specific examples only. The cyclic amide group may be one derived from a monocyclic or condensed heterocyclic ring. The condensed heterocylcic ring is preferably one formed by condensation with a phenyl ring. In this case, the phenyl ring may be substituted with a lower alkyl group having 1 to 6 carbon atoms, preferably a methyl group, or a lower alkoxy group having 1 to 6 carbon atoms, preferably a methoxy group. Preferable examples of the monovalent group include the following groups:

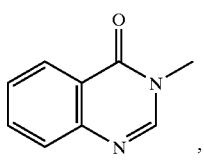
(a)

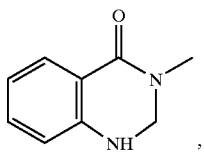
(b)

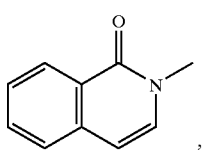
(c)

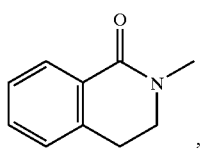
(d)

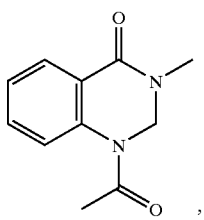
(e)

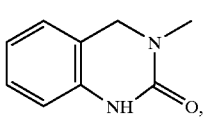
(f)

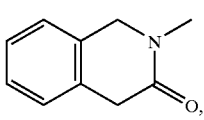
(g)

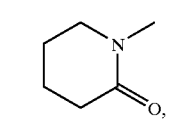
(h)

-continued

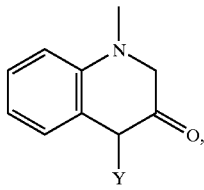
(i)

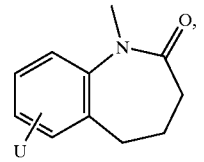
(j)

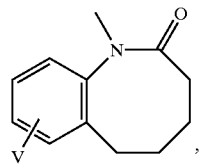
(k)

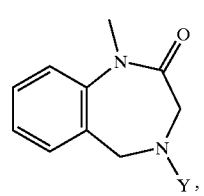
(l)

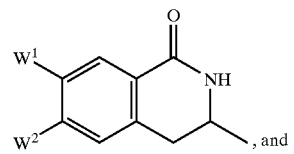
(m)

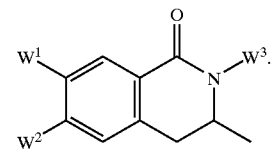
(n)

In the above formulae, Y's in the formulae (i) and (l) are each a hydrogen atom or a lower alkyl group, V in the formula (k) is a hydrogen atom or a lower alkoxy group, $W^1$ and $W^2$ in the formulae (m) and (n) are each a hydrogen atom, a lower alkyl group, or a lower alkoxy group and $W^3$ is a hydrogen atom or a lower alkyl group.

The right-hand ring in each of the formulae (j) and (l) is a seven-membered ring, while the right-hand ring in the formula (k) is an eight-membered ring.

The most preferable examples of the above-defined $R^1$ include a monovalent group derived from an indanone having an unsubstituted or substituted phenyl group and a monovalent group derived from a cyclic amide compound.

The most preferable examples of the above-defined X include a group represented by the formula $—(CH_2)_n—$, a group having an amide group, and groups represented by the above formulae wherein n is 2. Therefore, it is most preferable that any portion of a group represented by the formula $R^1=X—$ have a carbonyl or amide group.

The substituents involved in the expressions "a substituted or unsubstituted phenyl group" and "a substituted or unsubstituted arylalkyl group" in the above definition of $R^2$ are the same as those described in the above items (1) to (8) of the definition for $R^1$.

The term "arylalkyl group" is intended to mean an unsubstituted benzyl or phenethyl group, etc.

Specific examples of the pyridylmethyl group include 2-pyridylmethyl, 3-pyridylmethyl, and 4-pyridylmethyl groups.

Preferable examples of $R^2$ include benzyl and phenethyl groups. The symbol === means either a single or a double bond. This bond is a double bond only when $R^1$ is the above-described divalent group (III) derived from an indanone having an unsubstituted or substituted phenyl ring, while it is a single bond in other cases.

Moreover, the compounds of the present invention may have an asymmetric carbon atom depending upon the kind of the substituent and, therefore, have stereoisomers. They are, of course, within the scope of the present invention.

When $R^1$ has an indanone skeleton, the compound of the present invention has an asymmetric carbon atom and, therefore, may have stereoisomers, optical isomers, diastereomers, etc. All of these isomers are within the scope of the present invention.

In the present invention, the term "pharmacologically acceptable salt" includes those of inorganic acids, such as hydrochloride, sulfate, hydrobromide, and phosphate, and those of organic acids, such as formate, acetate, trifluoroacetate, methanesulfonate, benzenesulfonate, and toluenesulfonate. Further, when a certain kind of substituent is selected, the compound of the present invention may form, e.g., alkali metal salts such as a sodium or potassium salt, alkaline earth metal salts such as a calcium or magnesium salt, organic amine salts such as a salt with trimethylamine, triethylamine, pyridine, picoline, dicyclohexylamine, or N,N'-dibenzylethylenediamine.

In practicing the methods of the invention, the acetylcholinesterase inhibitor compounds of the present invention may be orally or parenterally administered. In general, they are parenterally administered in the form of injections, such as intravenous, subcutaneous, and intramuscular injections, suppositories, or sublingual tablets. The dose will vary depending upon the symptoms, age, sex, weight, and sensitivity of patients, method of administration, time and intervals of administration and properties, dispensing, and kind of pharmaceutical preparations, kind of effective ingredients, etc., so that there is no particular limitation with respect to the dose. Normally the compound may be administered in a dose of about 0.1 to 300 mg, preferably 1 to 100 mg, per day per patient, ordinarily in one to four portions.

Pharmaceutical preparations in the dosage form of, e.g., injections, suppositories, sublingual tablets, tablets, and capsules are prepared according to methods which are commonly accepted in the art.

In preparing injections, the effective ingredient is blended, if necessary, with a pH modifier, a buffer, a suspending agent, a solubilizing agent, a stabilizer, a tonicity agent, a preservative, etc., followed by preparation of an intravenous, subcutaneous, or intramuscular injection according to an ordinary method. In this case, if necessary, it is possible to lyophilize these preparations according to an ordinary method.

Examples of the suspending agents include methylcellulose, Polysorbate 80, hydroxyethylcellulose, acacia, powdered tragacanth, sodium carboxymethylcellulose, and polyoxyethylene sorbitan monolaurate.

Examples of the solubilizing agent include polyoxyethylene hydrogenated castor oil, Polysorbate 80, nicotinamide, polyoxyethylene sorbitan monolaurate, Macrogol, and an ethyl ester of castor oil fatty acid.

Examples of the stabilizer include sodium sulfite, sodium metasulfite, and ether, and examples of the preservative include methyl p-hydroxybenzoate, ethyl p-hydroxybenzoate, sorbic acid, phenol, cresol, and chlorocresol.

The compounds of the methods of the present invention may be prepared by various processes. A representative process for the synthesis of the compound 1-benzyl-4-[(5,6-dimethoxy-1-indanone)-2-yl]-methylpiperidine hydrochloride is detailed below as Example 1. Other representative processes for preparing the compounds used in the methods of the present invention can be found in U.S. Pat. No. 4,895,841, incorporated herein by reference in its entirety.

EXAMPLE 1

Synthesis of Donepezil Hydrochloride 1-benzyl-4-((5,6-dimethoxy-1-indanon)-2-yl) methylpiperidine A. Preparation of First Precursor 1-benzyl-4-piperidine-carboaldehyde having the formula:

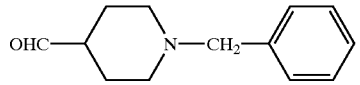

was prepared in the following way.

26 grams of methoxymethylene-triphenylphosophonium chloride was suspended in 200 ml of anhydrous ether. A 1.6M solution in hexane of n-butyl lithium was added dropwise to the suspension at room temperature. The mixture was stirred at room temperature for 30 minutes and cooled down to 0° C. Then 30 ml of a solution in anhydrous ether of 14.35 g of 1-benzyl-4-piperidone was added to the mixture. It was stirred at room temperature for 3 hours and filtrated to remove the insolubles. The filtrate liquid was concentrated at a reduced pressure. The obtained concentrate was dissolved in ether and extracted with 1N hydrochloric acid. An aqueous solution of sodium hydroxide was added to the extract to give a pH value of 12, followed by extraction with methylene chloride. The extract was dried with magnesium sulfate and concentrated at a reduced pressure. The residue was purified with a column filled with silica gel to obtain 5.50 g of an oil with a yield of 33 percent.

The oil was incorporated into 40 ml of methanol and 40 ml of 1N hydrochloric acid was added to the solution. It was heated so as to reflux for 3 hours and then concentrated at a reduced pressure. The residue was dissolved in water. An aqueous solution of sodium hydroxide was added to the solution to give a pH value of 12 and the solution was extracted with methylene chloride. The extract was washed with saturated salt solution and dried with magnesium sulfate. It was further concentrated at a reduced pressure and the residue was purified in a column charged with silica gel. 2.77 g of the intended compound was obtained with a yield of 54 percent. In analysis, its molecular formula was found to be $C_{13}H_{17}NO$ and $^1$H-NMR ($CDCl_3$)δ, 1.40–2.40 (7H, m), 2.78 (2H, dt), 3.45 (2H, S), 7.20 (5H, S), 9.51 (1H, d).

This compound may also be produced according to the methods shown in (1) Arm. Kim. Zh., 36(9), 614–17 (1983) by R. A. Kuroyan, A. I. Markosyan, G. M. Snkhchyan and S. A. Vartangan and (2) Ind. Chim. Belge, 32, 64–5 (1967) by B. Hermans and P. Van Daele.

B. Preparation of Second Precursor

1-Benzyl-4-[(5,6-dimethoxy-1-indanon)-2-ylideny]-methylpiperidine hydrochloride:

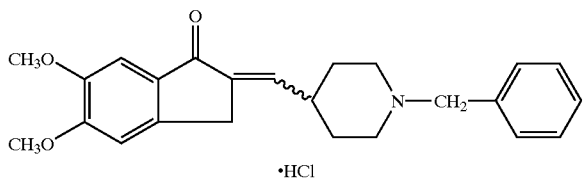

·HCl

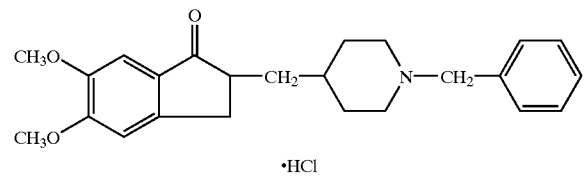

·HCl was prepared via a reaction conducted in an argon atmosphere.

2.05 ml of diisopropylamine was added to 10 ml of anhydrous THF, followed by addition of 9.12 ml of a 1.6M solution of n-butyllithium in hexane at 0° C.

The mixture was stirred at 0° C. for 10 min and then cooled to −78° C., and a solution of 2.55 g of 5,6-dimethoxy-1-indanone in 30 ml of anhydrous THF and 2.31 ml of hexamethyl-phosphoric amide were added. The mixture was stirred at −78° C. for 15 min, and a solution of 2.70 g of 1-benzyl-4-piperidinecarboaldehyde in 30 ml of anhydrous THF was added. The temperature of the mixture was gradually raised to room temperature, followed by stirring for 2 hr. An aqueous 1% ammonium chloride solution was added, and the organic phase was separated. The water phase was extracted with ethyl acetate, and the organic phases were combined with each other. The combined organic phase was washed with a saturated saline solution, dried over magnesium sulfate, and concentrated in vacuo. The resulting residue was purified on a silica gel column (methylene chloride:methanol=500:1–100:1). The eluate was concentrated in vacuo, and the residue was dissolved in methylene chloride. A 10% solution of hydrochloric acid in ethyl acetate was added to the resulting solution, followed by concentration in vacuo to obtain a crystal, which was recrystallized from methanol/IPE to obtain 3.40 g (yield: 62%) of the title compound having the following properties: m.p. (°C.): 237°–238° C. (dec.) elementary analysis: $C_{24}H_7NO_3 \cdot HCl$. C (69.64% calculated; 69.51% found). H (6.82% calculated; 6.78% found). N (3.38% calculated; 3.30% found).

C. Donepezil Hydrochloride

1-Benzyl-4-[(5,6-dimethoxy-1-indanon)-2-yl]-methylpiperidine hydrochloride (donepezil hydrochloride):

was prepared from the precursors as follows.

0.4 g of 1-benzyl-4-[(5,6-dimethoxy-1-indanon)-2-ylidenyl]methylpiperidine was dissolved in 16 ml of THF, followed by addition of 0.04 g of 10% palladium-carbon. The mixture was hydrogenated at room temperature under atmospheric pressure for 6 hr. The catalyst was filtered off, and the filtrate was concentrated in vacuo. The residue was purified by making use of a silica gel column (methylene chloride:methanol=50:1). The eluate was concentrated in vacuo, and the residue was dissolved in methylene chloride. A 10% solution of hydrochloric acid in ethyl acetate was added to the resulting solution, followed by concentration in vacuo to obtain a crystal, which was recrystallized from methanol/IPE to obtain 0.36 g (yield: 82%) of the title compound having the following properties: m.p. (°C.): 211°–212° C. (dec.) elementary analysis: $C_{24}H_{29}NO_3 \cdot HCl$. C (69.30% calculated; 69.33% found). H (7.27% calculated; 7.15% found). N (3.37% calculated; 3.22% found).

EXAMPLE 2

Utility for Attention Disorders

The effects of the cholinesterase inhibitor donepezil hydrochloride on the cognitive performance of patients with Alzheimer's disease was evaluated in a 15-week, multi-center, double-blind, placebo-controlled trial of 458 patients. This study administered donepezil hydrochloride (5 or 10 mg) or placebo to patients in a blinded fashion for a period of 24 weeks, followed by 3 weeks of single-blind placebo. Psychometric evaluations were conducted at 3 week intervals during the study. One hundred fifty patients received 5 mg doses, 156 received 10 mg doses, and 156 received a matching placebo. Effects on attention were evaluated using the Attention/Calculation element of the Mini-Mental Status Examination (MMSE). Improvement in attention and calculation performance is indicated by positive values, deterioration is indicated by negative values. The analysis of this domain of the study is presented in Table 1.

TABLE 1

MMSE-Attention and Calculation Domain
Intent to Treat Population Study-301

| Week | Placebo (A) | Donepezil HCl 5 mg/day (B) | Donepezil HCl 10 mg/day (C) | Pair-wise Comparison/p-values | | | |
|---|---|---|---|---|---|---|---|
| | | | | Overall | A vs. B | A vs. C | B + C vs. A |
| Baseline [Adjusted Mean (SE)] | 3.351 (0.146) | 3.468 (0.143) | 3.247 (0.143) | 0.5515 | | | |
| Week 12 | −0.123 (0.110) | 0.153 (0.109) | 0.248 (0.116) | 0.0417* | 0.0647 | 0.0164* | 0.0137 |
| Endpoint | −0.94 (0.106) | 0.66 (0.106) | 0.354 (0.107) | 0.0422* | 0.2728 | 0.0121* | 0.037* |

*Statistically significant change from baseline $0.001 < p < 0.05$

A 30-week, multi-center, double-blind, placebo-controlled trial of 458 patients was also conducted in patients with Alzheimer's disease. As in the first study, donepezil hydrochloride (5 or 10 mg) or placebo was administered to patients in a blinded fashion for a period of 24 weeks followed by 6 weeks of single-blind placebo. Psychometric evaluations were conducted at 6 week intervals during the study. One hundred fifty four patients received 5 mg doses, 154 received 10 mg doses, and 150 received a matching placebo. Effects on attention were evaluated using the Attention/Calculation element of the Mini-Mental Status Examination (MMSE). Improved attention and calculation performance is indicated by positive values, deterioration is indicated by negative values. The analysis of this domain of the study is presented in Table 2.

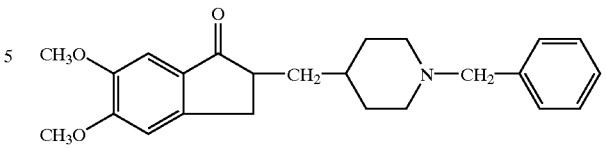

or a stereoisomer thereof.

2. The method of claim 1, wherein the compound of formula (I) is:

TABLE 2

MMSE-Attention and Calculation Domain
Intent to Treat Population Study-302

| Week | Placebo (A) | Donepezil HCl 5 mg/day (B) | Donepezil HCl 10 mg/day (C) | Overall | A vs. B | A vs. C | B + C vs. A |
|---|---|---|---|---|---|---|---|
| Baseline [Adjusted Mean (SE)] | 3.351 (0.158) | 3.468 (0.143) | 3.085 (0.164) | 0.734 | | | |
| Week 12 | −0.55 (0.117) | 0.153 (0.109) | 0.361 (0.123) | 0.0235* | 0.0316* | 0.0113* | 0.0067* |
| Week 24 | −0.187 (0.126) | 0.116 (0.128) | 0.160 (0.143) | 0.1086 | 0.0811 | 0.0624 | 0.0354* |
| Endpoint | −0.216 (0.117) | 0.66 (0.106) | 0.070 (0.121) | 0.1346 | 0.0855 | 0.0823* | 0.0454* |

*Statistically significant change ftom baseline $0.001 < p < 0.05$

Beneficial effects of donepezil hydrochloride on attention were also observed in a study of healthy volunteers who received single 5 or 10 mg daily doses for a total of 3 weeks. One of these subjects had been suffering from a disorder of attention since childhood. He reported that he was able to concentrate better during treatment. As a result of his increased concentration, he was able to complete a music project, which would normally have required more time, in one sitting. A second volunteer reported that he was less distracted and was able to concentrate on specific tasks longer during treatment with donezipil hydrochloride. These benefits wore off after treatment was discontinued.

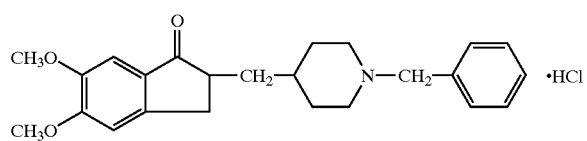

or a stereoisomer thereof.

3. The method of claim 1, wherein the compound of formula (I) is administered in a daily dose of from about 0.1 mg to about 100 mg.

4. The method of claim 3, wherein the compound of formula (I) is administered in a daily dose of from about 1 mg to about 100 mg.

5. The method of claim 4, wherein the compound of formula (I) is administered in a daily dose of from about 5 mg to about 10 mg.

6. The method of claim 5, wherein the compound of formula (I), is administered in a daily dose of about 5 mg.

7. The method of claim 5, wherein the compound of formula (I) is administered in a daily dose of about 10 mg.

8. The method of claim 1, further comprising administering a pharmaceutically acceptable carrier.

9. The method of claim 1, wherein the human is a child.

10. The method of claim 1, wherein the human is an adult.

11. A safe and effective method for treating attention deficit hyperactivity disorder in a human in need thereof comprising administering an effective amount of donepezil or a pharmaceutically acceptable salt thereof.

12. The method of claim 11, comprising administering an effective amount of donepezil hydrochloride.

Collectively, these results indicate that the administration of cholinesterase inhibitors, and in particular the compounds of the invention, surprisingly improves attention in humans, including persons with impaired memory such as Alzheimer's patients, healthy volunteers given a task to perform, and persons suffering from disorders of attention such as ADD.

What is claimed is:

1. A method for treating attention deficit hyperactivity disorder in a human in need thereof comprising administering an effective amount of a compound of formula (I) or a pharmaceutically acceptable salt thereof, wherein the compound of formula (I) is:

13. A safe and effective method for treating attention deficit hyperactivity disorder in a human in need thereof comprising administering an effective amount of a stereoisomer of donepezil or a pharmaceutically acceptable salt thereof.

14. The method of claim 13, comprising administering an effective amount of a stereoisomer of donepezil hydrochloride.

* * * * *